United States Patent [19]

Phillipps et al.

[11] 4,197,296
[45] Apr. 8, 1980

[54] ANDROSTANES

[75] Inventors: Gordon H. Phillipps, Wembley; George B. Ewan, Northolt, both of England

[73] Assignee: Glaxo Group Limited, London, England

[21] Appl. No.: 946,087

[22] Filed: Sep. 26, 1978

Related U.S. Application Data

[63] Continuation-in-part of Ser. No. 780,674, Mar. 23, 1977.

[30] Foreign Application Priority Data

Oct. 3, 1977 [GB] United Kingdom ............... 41027/77

[51] Int. Cl.$^2$ ...................... C07J 71/00; A61K 31/58
[52] U.S. Cl. ............................ 424/241; 260/239.55 C; 260/239.55 R; 260/397.5; 260/397.3; 260/397.45
[58] Field of Search ................... 424/241; 260/397.46, 260/239.55, 397.45, 397.5

[56] References Cited

U.S. PATENT DOCUMENTS

| 3,033,855 | 5/1962 | Berg et al. | 260/397.45 |
| 3,869,451 | 3/1975 | Phillipps et al. | 260/397.45 |
| 3,943,124 | 3/1976 | Phillipps et al. | 260/397.45 |
| 3,983,111 | 9/1976 | Phillipps et al. | 260/397.45 |

FOREIGN PATENT DOCUMENTS

| 878069 | 9/1961 | United Kingdom | 260/397.45 |
| 924421 | 4/1963 | United Kingdom | 260/397.45 |

OTHER PUBLICATIONS

Pelah et al., "JACS," (1965) 87 (3), pp. 574–580.
Marples, "J. Chem. Soc.," Perkin Trans I (1974), pp. 2219–2225, No. 19.

Primary Examiner—Elbert L. Roberts
Attorney, Agent, or Firm—Bacon & Thomas

[57] ABSTRACT

Steroids of the androstane series are described which possess a 3α-hydroxy group, a 5α- or 5β- hydrogen atom, a 10- methyl group, an 11α- substituted amino group. The 17-position may be unsubstituted or substituted by a methyl or ethyl group in the β-configuration or by an oxo group, or there may be a 16β, 17β-epoxide group. A 2β-alkoxy group may optionally be present.

The compounds, particularly their salts, have anaesthetic activity.

13 Claims, No Drawings

ANDROSTANES

This application is a continuation-in-part of our prior copending application Ser. No. 780,674, filed Mar. 23, 1977.

This invention relates to anaesthetic steroids.

Many steroids possessing anaesthetic activity are now known, these mostly being 3α-hydroxy 5α- or Δ⁴-compounds in the 17α-unsubstituted 20-oxo-pregnane and androstane series, the best compounds often having an 11-oxo group. These compounds are mostly insufficiently soluble in water, and it has been necessary to formulate them for administration in aqueous solutions of parenterally acceptable non-ionic surface active agents as for example described in British patent specification No. 1317184 with regard to the important anaesthetic 3α-hydroxy-5α-pregnane-11,20-dione. Anaesthetic steroids are also known which possess water-solubilising groups at various positions on the steroid nucleus, for example at the 2β, 11β, 3α or 21-position in a pregnane or the 11β or 17β-position in an androstane, but the introduction of the water-solubilising group has frequently resulted in a fall in activity or stability.

We have now found very interesting anaesthetic activity in a group of 3α-hydroxy 5α- and 5β-steroids possessing a dialkylamino group at the 11α-position, particularly in the water soluble salts of these compounds with acids.

These compounds are of the formula

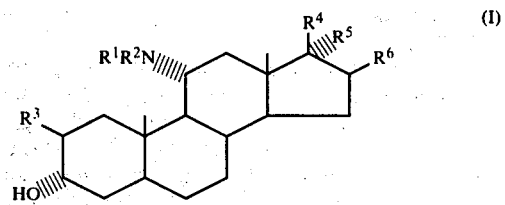

wherein:
one of $R^1$ and $R^2$ is a methyl group, the other group being a $C_{1-4}$ alkyl group, or $R^1$ and $R^2$ are both ethyl groups;
$R^3$ is a hydrogen atom or a $C_{1-4}$ alkoxy group; and
$R^4$ is a hydrogen atom or a methyl or ethyl group and $R^5$ and $R^6$ are hydrogen atoms, or $R^4$ and $R^6$ together represent an epoxide grouping and $R^5$ is a hydrogen atom, or $R^4$ and $R^5$ together represent an oxo group and $R^6$ is a hydrogen atom;
and the acid addition salts thereof.

In the tests we have carried out, the compounds of the invention have been shown generally to be good anaesthetics, usually giving rapid induction of anaesthesia when administered intravenously. The water soluble salts are particularly important in that they can be formulated in aqueous solution. The aqueous solutions of the water soluble salts have in general been found to be sufficiently stable. The compounds of the invention are of use for inducing anaesthesia which is to be maintained for example by an inhalation anaesthetic, such as ether, halothane, nitrous oxide or trichloroethylene. The compounds may also be capable of maintaining anaesthesia to a sufficient degree to enable surgical operations to be conducted without the aid of an inhalation anaesthetic, the anaesthesia being maintained if necessary by repeated or continuous administration. The compounds may have other desirable central nervous system depressant activities, for example they may be of use as sedatives.

Compounds having a 2β($R^3$)-substituent are particularly important in the 5α-series, examples of such substituents being a methoxy, ethoxy, propoxy, iso-propoxy or butoxy group. Compounds in the 5α-series in which $R^3$ is an ethoxy group are particularly preferred.

$R^3$ is preferably a hydrogen atom when a 5β-hydrogen atom is present.

One of $R^1$ and $R^2$ may be a straight or branched chain $C_{1-4}$ alkyl group such as a methyl, ethyl, propyl iso-propyl, butyl or iso-butyl group.

$R^1$ and $R^2$ are preferably both methyl groups. Compounds in the 5α-series are preferred. Compounds possessing a 17-oxo group in the 2β-alkoxy 5α-series are preferred.

As indicated above, the ability of the bases of the invention to form water soluble acid addition salts is particularly important. Thus, the compounds of the invention in the form of their bases can be formulated simply in aqueous acidic solution.

Examples of suitable salts are hydrochlorides, hydrobromides, phosphates, sulphates, p-toluenesulphonates, methanesulphonates, citrates, tartrates, acetates, ascorbates, lactates, maleates, succinates, tricarballylates, glutarates, aconitates, citraconates, mesaconates, salicylates and glutaconates. The citrate and hydrochloride salts are particularly preferred for use as anaesthetics.

When these salts are used as anaesthetics they should by physiologically acceptable at the dosage at which they are administered. Other salts may, however, be of use in for example isolation of the product from a synthetic reaction.

Preferred compounds are:
11α-N,N-dimethylamino-2β-ethoxy-3α-hydroxy-5α-androstan-17-one;
11α-N,N-dimethylamino-2β-ethoxy-17β-methyl-5α-androstan-3α-ol;
11α-N,N-dimethylamino-2β-ethoxy-5α-androstan-3α-ol;
11α-N,N-dimethylamino-16β,17β-epoxy-2β-ethoxy-5α-androstan-3α-ol; and
11α-N,N-dimethylamino-17β-methyl-5α-androstan-3α-ol;

and the physiologically acceptable water soluble salts of these compounds. These compounds, and particularly the first compound listed, have shown good activity in our tests in the form of their citrate salts in aqueous solutions.

PHARMACEUTICAL FORMULATIONS

The invention also includes the use of the compounds of formula (I) and their salts in the treatment of the human or animal body, e.g. for inducing anaesthesia.

The compounds of the invention may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises a composition for parenteral administration comprising one or more compounds in accordance with the invention in a parenterally acceptable vehicle.

When the compounds are sufficiently soluble in water (e.g. the salts), they may be presented in aqueous injection vehicles. The preparation of suitable solutions by bringing the free bases into solution in aqueous acid is described below. For induction anaesthesia, these solutions will usually contain 0.1–4.0% (conveniently 0.2–2%) w/v of the active compound, but stronger solutions may be prepared with the more soluble salts. If desired, the free base and the acid required for salt formation may be packed separately in two-pack form for formulation as and when needed. Alternatively the steroid salt and the aqueous injection vehicle may be packed separately in two-pack form.

Although the compounds of the invention are preferably formulated as simple aqueous solutions of their salts, the free bases or salts may also be formulated in an aqueous solution of a parenterally acceptable non-ionic surface active agent in the same way (and using the same proportions of materials) as described in our British patent specification No. 1317184 for $3\alpha$-hydroxy-$5\alpha$-pregnane-11,20-dione. The simple aqueous solutions have the advantage for example of avoiding anaphylactoid responses in surfactant-sensitive subjects.

The aqueous solutions may be adjusted in tonicity, for example with sodium chloride.

The anaesthetic solutions according to the invention are generally administered by intravenous injection although in certain cases (e.g. with children or animals) intramuscular injection might be preferred.

The simple aqueous solutions of the salts may also be administered subcutaneously.

As is usual in the case of anaesthetics, the quantity of steroid used to induce anaesthesia depends upon the weight of the individual to be anaesthetised. For intravenous administration in the average man a dose of from 0.1 to 8.0 mg/kg will in general be found to be satisfactory to induce anaesthesia, the preferred dose being within the range of from 0.2 to 4.0 mg/kg. The dose will naturally vary to some extent, dependent upon the physical condition of the patient and the degree and period of anaesthesia required.

If it is desired to maintain prolonged anaesthesia, repeated doses of the above solutions may be used, such repeated doses being generally either of the same order or lower than the original dose. Alternatively continuous administration may be undertaken using solutions containing 0.01–0.4% (preferably 0.02–0.2) w/v of the active compound at for example a rate of 0.0125–0.2 (e.g. 0.025–0.1) mg/kg/min. Continuous administration may also be used to produce sedation for prolonged periods.

Where the anaesthetic solutions are administered intramuscularly or subcutaneously, higher doses are generally necessary.

COMPOUND PREPARATION

The compounds of the invention may be prepared by a number of different methods, using generally known techniques. Suitable methods are described below.

1. Alkylating an unsubstituted or mono-substituted $11\alpha$-amine.

This reaction may be performed by reacting a corresponding compound of formula (I) in which either or both of $R^1$ and $R^2$ is hydrogen with a compound of the formula $R^1X$ where X is a readily displaceable group such as halide (e.g. iodide), a hydrocarbylsulphonyloxy group (e.g. toluene-p-sulphonyloxy), hydrocarbyloxysulphonyloxy (e.g. methoxysulphonyloxy) or a dialkoxyphosphonyloxy group (e.g. dimethoxyphosphonyloxy). The reaction is preferably carried out in the presence of a base (e.g. potassium carbonate or silver oxide) in solution at any suitable temperature from ambient to reflux, conveniently at ambient temperature. An excess of the compound $R^1X$, e.g. methyl iodide, may be used as the reaction solvent, but there are many other alternative solvents such as halogenated hydrocarbon solvents (e.g. methylene chloride), alkanols (e.g. ethanol or methanol) or acetonitrile.

When a N-mono-substituted starting material is used, the reaction can produce N,N-di-substituted compounds of the invention in which $R^1$ and $R^2$ are either the same or different groups.

The N-mono-substituted starting materials may be prepared in similar manner by reacting a compound of formula I in which both $R^1$ and $R^2$ are hydrogen atoms with a compound of formula $R^1X$ as described above.

When a 17-oxo group is present in the starting material, this may be protected as described below as a 17-ketal group. Such protection is not necessary in the N-substitution reaction, but a 17-ketal group is often present as a result of the earlier stages in the preparative sequence. Isolation of the product of the N-substitution reaction frequently involves acidic conditions which also serve to regenerate the desired 17-oxo group.

The $11\alpha$-amino starting materials required for this reaction may for example be prepared by stereoselectively reducing the corresponding 11-oxime. This reduction may be effected with an alkali or alkaline earth metal reducing agent in an alcohol and/or an amine and/or ammonia, e.g. sodium in n-propanol, if desired in the presence of a suitable solvent, e.g. tetrahydrofuran, at any suitable temperature up to and preferably at reflux.

The 11-oximes may themselves be prepared from the corresponding 11-oxo compounds in which the 17-oxo group (if present) is protected as a ketal group. The 11-oxo compound may for example be reacted with hydroxylamine under strongly alkaline conditions in aqueous alcohol (e.g. ethanol), preferably at reflux. When other oxo groups are absent, the reaction may be carried out under acidic conditions (ca, pH 4), e.g. in buffered pyridine.

The severe conditions used in the reduction of the 11-oxime make it necessary or desirable that the $16\beta,17\beta$-epoxide group (where desired) should be introduced after the formation of the $11\alpha$-amino group. In introducing this substituent it can be desirable to protect the $11\alpha$-amino group. Conventional amine protection methods may be used, e.g. acylation (e.g. with trifluoroacetic or formic acid or a reactive derivative thereof) or silylation.

2. A corresponding $11\alpha$-alkanoylamino steroid (i.e. in which one of $R^1$ and $R^2$ is as defined above and the other is an alkanoyl group) may be reduced, for example with lithium aluminium hydride in an ether solvent (e.g. tetrahydrofuran or dimethoxyethane) at any suitable temperature up to reflux. The starting material may possess a 17-ketal group, which should subsequently be converted into a 17-oxo group, or a $3\alpha$-esterified hydroxy group, which will be converted to a $3\alpha$-hydroxy group in the reaction.

The alkanoylamino starting materials may be prepared by acylation of an appropriate $11\alpha$-mono-substituted amino compound (or a 17-ketal derivative thereof), for example with the appropriate carboxylic acid (or a reactive derivative thereof, e.g. an acid halide, ester or anhydride), if desired in the presence of an acid binding agent (e.g. pyridine). The $3\alpha$-hydroxy group will be acylated in this reaction and if desired may be regenerated by treatment with a base before the reduction. If the 11-alkanoylamino compound possesses a 3-oxo group, this may then be reduced to form the desired 3α-hydroxy group.

3. Opening of a corresponding 2α,3α-epoxide.

This reaction may be used to prepare the 2β-alkoxy 5α-compounds. The general method of preparing 2β-compounds by this route is described in our British patent specification No. 1376892. Thus in general the reaction comprises treatment of the corresponding 2α,3α-epoxide with an alcohol $R^3H$ under acidic conditions (in the presence of an added acid catalyst, e.g. sulphuric acid, perchloric acid or boron trifluoride) or a compound which produces the anion $(R^3)^-$ (where $R^3$ is an alkoxy group), and then (when the initial product possesses a deprotonated 3α-hydroxy group) treating the product with a source of protons (e.g. aqueous ammonium chloride) to form the 3α-hydroxy group. Examples of reagents which produce $(R^3)^-$ anions are alkali metal alkoxides. The reaction is preferably carried out under anhydrous conditions in a suitable solvent (e.g. a hydrocarbon or an ether) at any suitable temperature up to reflux.

The starting materials required for this reaction may for example be prepared by first introducing the desired 11α-substituted amino group (e.g. by the method of reaction 1 above) using a $\Delta^2$-starting material, then forming a salt (e.g. with toluene-p-sulphonic acid) and the epoxidising the $\Delta^2$-compound with a peracid, finally regenerating the free base. $\Delta^2$-Compounds may be prepared by formation of the 3-methanesulphonate and subsequent elimination of methanesulphonic acid.

4. A corresponding 11α-amino or 11α-mono-substituted amino compound (or a 17-ketal thereof) can be reductively alkylated with an appropriate mono-carbonyl compound in the presence of a reducing agent. For example, with 11α-amino compounds the use of mono-carbonyl compounds, such as formaldehyde or acetaldehyde, can provide the 11α-dimethyl or -diethyl amines. The reducing agents which may be used are those generally known for the reduction of imines, examples being formic acid (e.g. at any suitable temperature up to 100°-120° C., for example from room temperature up to 100°, and using the carbonyl compound as the reaction solvent, in the presence or absence of water), an alkali metal borohydride or cyanoborohydride (e.g. sodium borohydride or cyanoborohydride, using an alcohol such as ethanol as solvent, suitably at room temperature), iron pentacarbonyl or an alkali metal hydrogen iron carbonylate (e.g. $Fe(CO)_5$ or $MHFe(CO)_4$ where M is sodium or potassium, at any suitable temperature up to reflux using an ether such as tetrahydrofuran or an alcohol or aqueous alcohol as solvent), hydrogen in the presence of a metal catalyst (using an alcohol, e.g. ethanol, an ether, e.g. dioxan or an ester, e.g. ethyl acetate, as reaction solvent, conveniently at room temperature), or aluminium amalgam in the presence of water (conveniently at room temperature, and in the presence of an ether solvent such as tetrahydrofuran).

The metal catalyst may, for example, be a noble metal catalyst such as platinum, palladium or rhodium. The catalyst may be supported, e.g. on charcoal or kieselguhr. A homogeneous catalyst such as tristriphenylphosphine rhodium chloride may also be used. If the intermediate imino compound is sufficiently stable, it may if desired be isolated.

11α-N-Mono-substituted amino starting materials can be prepared in similar manner by reacting the corresponding 11α-amino compound with an appropriate aldehyde or ketone in the presence of a reducing agent as described above. Thus, for example, the use of formaldehyde, acetaldehyde or acetone can provide the 11α-N-methyl-,N-ethyl or N-iso-propyl amines respectively. Whether an 11α-N-mono- or N,N-disubstituted compound is obtained is dependent partly on the proportion of ketone or aldehyde used.

5. 2β-Unsubstituted 5α-steroids of the invention may be prepared from appropriate 3-oxo compounds by stereo-specific reduction, e.g. by the method of Browne and Kirk (J. Chem. Soc. C, 1969, 1653) or by the method of our British patent specification No. 1409239. The latter method preferably uses a pre-formed iridium catalyst reduction system. For example, a reduction system may be prepared from an iridium acid or salt (e.g. chloroiridic acid), a trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed by heating at reflux, e.g. for 16 to 72 hours, the reduction can be accomplished for example in 2-3 hours at reflux; longer times may be necessary at room temperature.

6. Reduction of a corresponding 3-oxo 5β-compound.

3α-Hydroxy 5β-steroids may be prepared by hydride reduction of the corresponding 3-oxo compound (in which a 17-oxo group, if present, is optionally protected), for example with sodium borohydride using an alcohol (e.g. ethanol) or pyridine as solvent.

7. Inversion of the 3-hydroxy group of a derivative of the corresponding 3β-hydroxy compound.

The starting material may be a corresponding compound possessing a readily displaceable 3β-group such as a hydrocarbylsulphonyloxy (e.g. p-toluenesulphonyloxy or mesyloxy) group, and the 3β-group may be displaced by hydrolysis (e.g. in acid conditions) to give the desired 3α-hydroxy compounds.

8. Reduction of the corresponding $\Delta^{16}$ compound.

Compounds in which $R^5$ and $R^6$ are hydrogen atoms may be prepared by hydrogenating the corresponding $\Delta^{16}$ compound in the presence of a hydrogenation catalyst (e.g. a palladium catalyst) in a suitable solvent (e.g. an alcohol, ether or ester). The reaction may be effected conveniently at or about room temperature and atmospheric pressure.

9. A 17β-methyl or ethyl group may be introduced by hydrogenation or an appropriate 17-methylene or ethylidene compound in the presence of a hydrogenation catalyst (e.g. a palladium catalyst) in a suitable solvent (e.g. an alcohol, ether or ester). The reaction may be effected conveniently at or about room temperature and atmospheric pressure.

The 17-methylene or ethylidene compounds required in this preparation may themselves be prepared by a Wittig reaction, by reacting a 17-oxo steroid with for example a suitable organo-phosphorus reagent, such as a methylene- or ethylidene-phosphorane (e.g. methylene- or ethylidene-triphenyl phosphorane), which is conveniently prepared in situ using a base (e.g. sodium hydride) in a solvent (such as dimethylsulphoxide or tetrahydrofuran) and a methyl or ethyl phosphonium salt (e.g. a methyl- or ethyl-triphenylphosphonium halide e.g. bromide or chloride).

10. Reduction of a 17-ketone.

Compounds in which $R^4$, $R^5$ and $R^6$ are hydrogen atoms may be prepared from a corresponding 17-ketone by a Wolff-Kishner reduction using hydrazine together with a base. Suitable bases include alkali metal hydroxides and alkoxides, such as sodium hydroxide and potassium tert-butoxide; suitable solvents include ethylene glycol and dimethylsulphoxide.

11. A 16β,17β-epoxide group may be introduced by treating a corresponding 17α-halo-(e.g. bromo- or chloro-) 16β-hydroxy-steroid with a base, e.g. an alkali metal or alkaline earth metal hydroxide, carbonate or bicarbonate (such as sodium hydroxide or potassium carbonate) in a suitable aqueous solvent (e.g. aqueous methanol). This is the preferred method of preparing the 16β,17β-epoxides.

The 17α-halo-16β-hydroxy-steroids may themselves be prepared from the corresponding $\Delta^{16}$-steroid by treatment with a source of positive halogen (e.g. N-bromo- or N-chlorosuccimimide) in the presence of an aqueous acid (e.g. aqueous perchloric acid) and in a suitable solvent (e.g. aqueous tetrahydrofuran).

12. Deketalisation of a corresponding 17-ketal.

As indicated above, it is frequently necessary or desirable to protect a 17-oxo group during the preparation of the androstanes of the invention, for example by ketalisation. The 17-oxo group may then be regenerated as the final step in the preparation. The ketal is preferably the corresponding 17,17-ethylenedioxy compound, and the 17-oxo group may be regenerated for example by hydrolysis in the presence of an acid (e.g. hydrochloric, sulphuric or acetic acid), or by exchange reaction with a ketone e.g. acetone in the presence of an acid catalyst, e.g. p-toluenesulphonic acid, at a temperature of 0°–100° C.

13. Deprotection of a corresponding compound having a protected 3α-hydroxy group.

This method is sometimes a necessary last stage in the preparation of the compounds of the invention in that the 3α-hydroxy group is often either deliberately protected or is formed in the esterified state by inversion from a 3β-alcohol with diethyl azodicarboxylate in the presence of an acid such as formic or benzoic acid and a phosphine such as triphenylphosphine). The group present at the 3α-position in the starting materials in this reaction may thus be an ester group, e.g. an alkanoyloxy group, and such esters may be hydrolysed to give the desired 3α-hydroxy compounds under acidic or basic conditions. Weakly basic conditions are generally most convenient (using for example an alkali metal bicarbonate in aqueous methanol at any suitable temperature up to reflux). Dilute mineral acids (e.g. perchloric acid in aqueous methanol) may also be used.

Alternatively, the starting material in this reaction may be a protected 3α-hydroxy compound such as a 3α-ether (e.g. 3α-tetrahydropyranyl ether) or a 3α-nitro-oxy compound. Such ether protecting groups may be removed by treatment with an aqueous acid, and such nitro-oxy groups may be removed by reduction, for example using zinc and acetic acid.

14. Salt formation.

Compounds of the invention are desirably used in the form of a salt, and thus salt formation by reaction of the base with an acid is particularly important.

A generally convenient method of forming the salts is to mix appropriate quantities of the free base and the acid in a mixture of water and a solvent for the base (e.g. an alcohol such as ethanol), removing the solvent (e.g. by evaporation) and then if desired dissolving the residue in water.

In some cases solid salts can be formed by treating the free base with acid (e.g. citric acid, HCl) in an anhydrous solvent, such as diethyl ether. In most cases it is possible to form an aqueous solution of the salt by simply mixing the free base with an aqueous acid. If desired one or more steroid bases and/or one or more acids may be used.

In these preparations, the base and the acid are not necessarily used in equivalent quantities. When the acid is a weak acid, an excess of the acid is sometimes desirable. In the preparation of aqueous solutions, in some cases for example it is found that an excess of the base may be used, implying that the free base is dissolved to some extent in the solution of the salt.

If desired the pH of the salt solution may subsequently be adjusted by addition of a base, e.g. sodium hydroxide and/or disodium hydrogen citrate.

The methods indicated above for preparing the compounds of the invention can be used as the last main step in a preparative sequence. The same general methods can be used for the introduction of the desired groups at an intermediate stage in the stepwise formation of the required compound, and it will be appreciated that these general methods can be combined in many different ways in such multi-stage processes, as will be apparent from the Examples below. Thus for example the desired 11α-substituted amino group may be formed either before or after the reduction of a 3-oxo group or 16,17-double bond, and either before or after the introduction of a substituent at the 17-position. The sequence of the reactions in multi-stage processes should of course be chosen so that the reaction conditions used do not affect groups in the molecule which are desired in the final product.

The 17-oxo steroids may be prepared by choice of starting materials of appropriate structure.

The $\Delta^{16}$ starting materials required in certain of the above reactions may be prepared from the corresponding 17-oxo steroid by treatment with toluene sulphonyl hydrazide in an inert solvent such as ethanol and decomposition, under aprotic basic conditions, of the tosylhydrazone thus formed (using for example methyl lithium in tetrahydrofuran).

The following Examples illustrate the invention. Temperatures are in °C. Melting points were determined on a Kofler block and are uncorrected. Optical rotations were determined at room temperature on solutions in chloroform (ca. 1% w/v). "Petroleum ether" and "petrol" refer to the fraction boiling at 60°–80° C. unless otherwise stated. "TLC" refers to thin layer chromatography.

PREPARATION 1

20-Oximino-5α-pregna-2,16-dien-11-one

A mixture of 5α-pregna-2,16-diene-11,20-dione (60 g), hydroxylammonium chloride (21 g) and anhydrous pyridine (240 ml) was left to stand at room temperature overnight before diluting with ice and water. The precipitate obtained was collected by filtration, washed with water and dried in vacuo at 80° (62 g.). Crystallisation from ethyl acetate afforded the title compound, m.p. 168°–182°, $[\alpha]_D$ +137°.

PREPARATION 2

5α-Androst-2-ene-11,17-dione

A solution of 20-oximino-5α-pregna-2,16-diene-11-one (60 g) in anhydrous pyridine (250 ml) was treated with 225 ml of a solution prepared from phosphorus oxychloride (55 ml) in anhydrous pyridine (250 ml) whilst maintaining the reaction temperature at '5° during addition of the reagent. The reaction mixture was then added to a solution of concentrated HCl (350 ml) in water (3 l). This mixture was stirred for 60 hours before collecting the precipitate by filtration. The precipitate was washed with water, dissolved in hot industrial methylated spirits and treated with 2 N HCl (50 ml) at room temperature. After one hour, the reaction mixture was diluted with water and the precipitate obtained was collected by filtration, washed with water and dried. (38.4 g). Crystallisation from methanol afforded the title compound, m.p. 188°–192°, $[\alpha]_D + 207°$.

PREPARATION 3

2α,3α-Epoxy-5α-androstane-11,17-dione

A mixture of 5α-androst-2-ene-11,17-dione (37.2 g), m-chloroperbenzoic acid (30 g) and chloroform (600 ml) was allowed to stand for 0.5 hour at room temperature before partitioning between chloroform and saturated aqueous $NaHCO_3$ solution. The organic phase was isolated and washed with water, dried and evaporated to a low volume. Addition of petroleum ether (b.p. 60°–80° C.) followed by refrigeration overnight afforded crystalline material (27.5 g). Recrystallisation from ethyl acetate-petroleum ether (b.p. 60°–80° C.) afforded the title compound, m.p. 166°–167°, $[\alpha]_D + 126°$.

PREPARATION 4

2β-Ethoxy-3α-hydroxy-5α-androstane-11,17-dione

A solution of 2α,3α-epoxy-5α-androstane-11,17-dione (5.0 g) in absolute ethanol (250 ml) was treated with eight drops of fuming $H_2SO_4$ at room temperature. After 45 minutes the reaction mixture was treated with aqueous $NaHCO_3$ and evaporated to low volume. Water was added to the mixture which was then refrigerated overnight. The precipitate was collected by filtration, washed with water and dried. Recrystallisation from water-ethanol afforded the title compound (2.1 g), m.p. 164°–167°, $[\alpha]_D + 114°$.

PREPARATION 5

2β-Ethoxy-3α-hydroxy-17-methylene-5α-androstan-11-one

Triphenylmethyl phosphonium bromide (7.5 g) was added to a suspension of sodium hydride (500 mg) in dry tetrahydrofuran (100 ml). The mixture was stirred at room temperature for 1.5 hours and then treated with 2β-ethoxy-3α-hydroxy-5α-androstane-11,17-dione (2.43 g). The mixture was refluxed for 1.5 hours, cooled and partitioned between ethyl acetate and water. The organic phase was washed with water, dried ($Na_2SO_4$) and evaporated in vacuo. Purification of the residue by chromatography over silica in ethyl acetate-petroleum ether (1:2) and crystallization from ether-petroleum ether afforded the titled compound (850 mg), m.p. 103°–108°, $[\alpha]_D + 25.5°$.

PREPARATION 6

2β-Ethoxy-3α-hydroxy-17-methylene-5α-androstan-11-one 11-oxime

A solution of 2β-ethoxy-3α-hydroxy-17-methylene-5α-androstan-11-one (1.75 g) in ethanol (50 ml) was added to a mixture of hydroxylamine hydrochloride (3.6 g) in 50% sodium hydroxide solution (14 ml) and the resulting suspension was stirred and refluxed for 35 hours. Most of the solvent was evaporated in vacuo and the residue was partitioned between ethyl acetate and water. Evaporation of the washed organic layer and crystallization of the residue from ethyl acetate afford the title compound (1.4 g), m.p. 97°–99°, $[\alpha]_D + 44.1°$.

PREPARATION 7

11α-Amino-2β-ethoxy-17-methylene-5α-androstan-3α-ol

Sodium (2.7 g) was added portionwise to a stirred and refluxing solution of 2β-ethoxy-3α-hydroxy-17-methylene-5α-androstan-11-one 11-oxime (1.7 g) in propanol (100 ml) under nitrogen. The cooled reaction mixture was diluted with water and the precipitated solid (1.43 g) was collected by filtration. A portion of this material (300 mg) was purified by partitioning between 2 N-hydrochloric acid and ether when the insoluble hydrochloride which precipitated was collected by filtration and again partitioned between ether and 2 N-sodium hydroxide solution. The organic layer was washed, dried ($Na_2SO_4$) and evaporated to give the title compound as a froth (180 mg), $[\alpha]_D + 1.6°$.

PREPARATION 8

17,17-Ethylenedioxy-2β-ethoxy-3α-hydroxy-5α-androstan-11-one

A solution of 2β-ethoxy-3α-hydroxy-5α-androstane-11,17-dione (8 g) in chloroform (80 ml) containing ethylene glycol (13 ml), ethyl orthoformate (8.3 ml) and p-toluene sulphonic acid (160 mg) was kept at room temperature overnight. The reaction mixture was washed with sodium bicarbonate solution and water, dried ($Na_2SO_4$) and evaporated in vacuo. Purification of the residual froth (8.6 g) by preparative thin layer chromatography over silica (acetone-petroleum ether 3:7) and crystallization from ethyl acetate-petroleum ether afforded the title compound m.p. 142°–145°, $[\alpha]_D + 18.2°$.

PREPARATION 9

2β-Ethoxy-17,17-ethylenedioxy-3α-hydroxy-5α-androstan-11-one 11-oxime.

2β-Ethoxy-17,17-ethylenedioxy-3α-hydroxy-5α-androstan-11-one (8.2 g) was added to hydroxylamine hydrochloride (15 g) in ethanol (500 ml) containing 44% sodium hydroxide solution (90 ml). After refluxing for 24 hours about half the solvent was evaporated in vacuo and the residue was diluted with water and extracted with ethyl acetate. The washed and dried ($Na_2SO_4$) organic solution was evaporated in vacuo to afford a froth which on crystallization from ethyl acetate-petroleum ether afforded the title compound m.p. 136°–140°, $[\alpha]_D + 41.1°$.

PREPARATION 10

11α-Amino-2β-ethoxy-3α-hydroxy-5α-androstan-17-one

Sodium (7.5 g) was added portionwise to a refluxing solution of 2β-ethoxy-17,17-ethylenedioxy-3α-hydroxy-5α-androstan-11-one 11-oxime (5.7 g) in propanol (400 ml) under nitrogen. Most of the solvent was evaporated in vacuo, water was added and the precipitated material was extracted into ethyl acetate. The washed extract was evaporated in vacuo and the residue was partitioned between ether and 2 N-hydrochloric acid. The aqueous layer was basified, extracted into ethyl acetate, washed, dried ($Na_2SO_4$) and evaporated to afford a froth which crystallized from ether to give the title compound m.p. 144°–148°, $[\alpha]_D+61.5°$.

PREPARATION 11

11α-N,N-Dimethylamino-2β-ethoxy-3α-hydroxy-5α-androstan-17-one 17-p-toluenesylphonylhydrazone A solution of 11α-N,N-dimethylamino-2β-ethoxy-3α-hydroxy-5α-androstan-17-one (2.0 g) in methanol (100 ml) was treated with p-toluenesulphonylhydrazide (1.0 g) and concentrated sulphuric acid (0.4 ml) and the mixture was refluxed under nitrogen. After 24 hours most of the solvent was removed in vacuo and the residue was partitioned between water and ether. The aqueous phase was basified with 2 N-sodium hydroxide and extracted with ether. The washed and dried organic extract was evaporated to yield a froth which was shown to contain an appreciable amount of starting material. The total product was retreated exactly as above to afford a crude product which was purified by preparative thin layer chromatography over silica (5% methanol in chloroform) and crystallization from ethyl acetate to give the title compound m.p. 209°–212° (decomp), $[\alpha]_D+9.4°$.

PREPARATION 12

11α-N,N-Dimethylamino-2β-ethoxy-5α-androst-16-en-3α-ol

A 1.5 M solution of methyl lithium in ether (20 ml) was added to a cooled solution of 11α-N,N-dimethylamino-2β-ethoxy-3α-hydroxy-5α-androstan-17-one 17-p-toluenesulphonylhydrazone (1.2 g) in dry tetrahydrofuran (100 ml). The mixture was kept at room temperature for three days and then most of the solvent was evaporated in vacuo. The residue was acidified with 2 N-hydrochloric acid, washed with ether, and the aqueous layer was then basified with 2 N-sodium hydroxide and extracted into ether. The washed and dried ($Na_2SO_4$) extract was evaporated in vacuo and the residue was purified by chromatography over silica (ethyl acetate-petroleum ether 1:1) and crystallization from aqueous methanol to give the title compound m.p. 51°–54°, $[\alpha]_D-23.8°$.

PREPARATION 13

17α-Bromo-11α-N,N-dimethylamino-2β-ethoxy-5α-androstane-3α,16β-diol

A solution of 11α-N,N-dimethylamino-2β-ethoxy-5α-androst-16-en-3α-ol (1.6 g) in tetrahydrofuran (40 ml) and water (16.5 ml) containing N-bromosuccinimide (1.05 g) and 60% perchloric acid (2 ml) was kept overnight at room temperature. The reaction mixture was partitioned between ethyl acetate and potassium carbonate solution and the organic extract was washed, dried ($Na_2SO_4$) and evaporated in vacuo. Purification of the residue by preparative thin layer chromatography over silica (ethyl acetate:petroleum ether 1:1) and crystallization from ether afforded the title compound m.p. 173°–174°, $[\alpha]_D-53.6°$.

PREPARATION 14

3α-Acetoxy-17-methylene-5α-androstan-11-one

Sodium hydride (0.330 g) was carefully added to sodium dried tetrahydrofuran (10 ml) under nitrogen. Methyl triphenylphosphonium bromide (4.9 g) was added as a suspension in dry tetrahydrofuran (30 ml) followed by 3α-acetoxy-5α-androstane-11,17-dione (1.2 g) also in dry tetrahydrofuran (20 ml). The reaction mixture was refluxed for ¾ hr. then cooled and poured into water. The product was extracted into ethyl acetate and the organic solution was washed with water, dried ($Na_2SO_4$) and evaporated. The residual oil was triturated with ether, the insoluble material was removed by filtration and the solid obtained by evaporation of the mother liquor was purified by chromatography over silica(ethyl acetate:petroleum ether 1:1) and recrystallisation from ether/petrol to give the title compound (0.695 g), m.p. 140°–1°, $[\alpha]_D+44°$.

PREPARATION 15

3α-Hydroxy-17-methylene-5α-androstan-11-one, 11-oxime

A solution of hydroxylamine was prepared by adding 50% sodium hydroxide solution (27 ml) to hydroxylamine hydrochloride (6.45 g) with cooling in an ice bath. This was added as a slurry to a refluxing solution of 3α-acetoxy-17-methylene-5α-androstan-11-one (4.33 g) in ethanol (100 ml). The reaction mixture was refluxed overnight then most of the ethanol was evaporated in vacuo and the precipitated crystals (3.831 g) were collected and recrystallised from ethyl acetate to give the title compound, m.p. 234°–6°, $[\alpha]_D+64°$.

PREPARATION 16

11α-Amino-17-methylene-5α-androstan-3α-ol

3α-Hydroxy-17-methylene-5α-androstan-11-one, 11-oxime (0.367 g) was refluxed in n-propanol under nitrogen. Sodium (0.360 g) cut into very small pellets was fed into the reaction mixture at intervals over the period of one hour until the reaction was complete. Methanol (1 ml) was was added to the reaction mixture which was then poured into a large volume of ice-water. The precipitate was filtered off and washed with water. This material was partitioned between 2 N-hydrochloric acid and ethyl acetate, the aqueous layer was basified with sodium hydroxide and re-extracted with ethyl acetate. Evaporation of the solvent gave a colourless oil (0.176 g) which on crystallisation from ethyl acetate/petrol gave the title compound (0.03 g) as fine white crystals, m.p. 144°–9°.

PREPARATION 17

3α-Acetoxy-17,17-ethylenedioxy-5α-androstan-11-one

A mixture of 3α-acetoxy-5α-androstane-11,17-dione (1.5 g), ethylene glycol (20 ml) and toluene-p-sulphonic acid (20 mg) in benzene (100 ml) was refluxed under a Dean and Stark head. After 7 hours when the reaction was essentially complete the cooled mixture was treated with pyridine (1 ml) and washed with water. Evaporation of the dried (MgSO$_4$) organic solution afforded the ketal (1.65 g) as a froth. Crystallization of a portion from a small volume of petroleum ether afforded the title compound m.p. 116°–123°.

PREPARATION 18

17,17-Ethylenedioxy-11-oximino-5α-androstan-3α-ol

3α-Acetoxy-17,17-ethylenedioxy-5α-androstan-11-one (1.0 g) was added to a solution of hydroxylamine prepared by addition of 50% aqueous sodium hydroxide (4 ml) to hydroxylamine hydrochloride (2 g) in ethanol (30 ml). After 17 hours reflux most of the solvent was evaporated in vacuo, the residue was diluted with water and the solid (836 mg) was collected by filtration. A portion was recrystallized from aqueous ethanol to afford the title compound m.p. 158°–159°.

PREPARATION 19

11α-Amino-17,17-ethylenedioxy-5α-androstan-3α-ol

A solution of 17,17-ethylenedioxy-11-oximino-5α-androstan-3α-ol (0.700 g) in propanol (20 ml) was refluxed under nitrogen. To this solution were added small pieces of sodium (total 0.8 g) over a period of 80 mins. The reaction mixture was evaporated to low volume then diluted with water. No precipitation occurred and the solution was partitioned between ethyl acetate and water. The ethyl acetate solution was washed with water ($\times 4$), dried (magnesium sulphate) and evaporated to a solid (0.575 g). Crystallisation from ethyl acetate/petrol gave colourless crystals of the title compound (0.396 g), m.p. 170°–171°, $[\alpha]_D - 36°$.

PREPARATION 20

(Z)-3α-Hydroxy-5α-pregn-17(20)-en-11-one

Sodium hydride (80% dispersion in oil; 1.0 g) was washed with petroleum ether and heated with dry dimethylsulphoxide at 70°–80° until a green solution was obtained. The solution was cooled to room temperature and then treated with ethyl triphenylphosphonium iodide (13.3 g) in dimethylsulphoxide (50 ml). 3α-Hydroxy-5α-androstane-11,17-dione (2.0 g) in distilled dimethylsulphoxide (40 ml) was added in one go and the mixture was heated to 40°–60°. After six hours the reaction mixture was poured into water and extracted into diethylether. Evaporation of the washed and dried extract afforded an oil which was purified by column chromatography using ethylacetate-petroleum ether (b.p. 40°–60°) (1:1) and crystallisation from ethyl acetate-petroleum ether to give title compound (824 mg), $[\alpha]_D + 29.0°$.

PREPARATION 21

(Z)-3α-Hydroxy-5α-pregn-17(20)-en-11-one oxime

A solution of (Z)-3α-hydroxy-5α-pregn-17(20)-en-11-one (10.264 g) in warm industrial methylated spirits (320 ml) was heated with hydroxylamine hydrochloride (3.25 g) and sodium hydroxide (5.123 g) in water (10 ml). The mixture was refluxed for 41 hours and, after addition of more hydroxylamine hydrochloride (15.35 g) in water (20 ml) and sodium hydroxide (25.04 g) in water (50 ml) refluxing was continued for a further 6 hours. The mixture was then poured into water and the crystalline material (10.419 g) collected by filtration. Crystallisation of a portion from aqueous ethanol afforded an analytical sample of title compound m.p. 233°–235°.

PREPARATION 22

(Z)-11α-Amino-5α-pregn-17(20)-en-3α-ol

A solution of (Z)-3α-hydroxy-5α-pregn-17(20)-en-11-one oxime (9.638 g) in propan-1-ol (200 ml) was refluxed under N$_2$ whilst Na (9.6 g) was added portionwise. When all of the Na had reacted, about 90 ml propan-1-ol was distilled and then the residue was poured into water, ice was added and the crystalline solid (9.19 g) was collected by filtration. A portion (6.17 g) was crystallised from ethanol-water to afford title compound (3.6 g), m.p. 118°–125°, $[\alpha]_D + 5.4°$.

PREPARATION 23

(Z)-11α-N,N-Dimethylamino-5α-pregn-17(20)-en-3α-ol

A suspension of (Z)-11α-amino-5α-pregn-17(20)-en-3α-ol, (550 mg) in 40% aqueous formaldehyde (4 ml) was treated with formic acid (0.3 ml) and the mixture was agitated until the steroid had dissolved. The solution was heated to ca 100° for 10 minutes, cooled and diluted with excess NaOH solution. The precipitated material was extracted into ethyl acetate, the extract was washed with water and then 2 N-HCl. The acid extract was washed with ethyl acetate, basified with NaOH and re-extracted with ethyl acetate. Evaporation of the washed organic extract afforded crystalline material which was purified by preparative TLC (5% methanol-chloroform) and crystallisation from methanol-water to afford title compound (309 mg), m.p. 59°–61°, $[\alpha]_D - 8.1°$.

PREPARATION 24

(Z)-2β-Ethoxy-3α-hydroxy-5α-pregn-17(20)-en-11-one

A mixture of 2β-ethoxy-3α-hydroxy-5α-androstane-11,17-dione (1.742 g), ethyl triphenylphosphonium iodide (6.27 g), sodium hydride (360 mg) and Na-dried tetrahydrofuran (100 ml) was stirred and refluxed under nitrogen. After 4.5 hours the reaction mixture was partitioned between ethyl acetate and water. The organic phase was isolated, washed with water, dried (Na$_2$SO$_4$) and evaporated to give an oil (4.0 g). Column-chromatography (ethyl acetate-petroleum ether) followed by preparative TLC (ethyl acetate-petroleum ether) and crystallisation from ethylacetate-petroleum ether afforded the title compound (110 mg), m.p. 172°–178°, $[\alpha]_D + 25°$.

PREPARATION 25

(Z)-2β-Ethoxy-3α-hydroxy-5α-pregn-17(20)-en-11-one-11-oxime

A solution of (Z)-2β-ethoxy-3α-hydroxy-5α-pregn-17(20)-en-11-one (710 mg) in refluxing ethanol (21 ml) was treated with a slurry of hydroxylammonium chloride (1.43 g) in 50% aqueous sodium hydroxide. After 24 hour refluxing, the cooled reaction mixture was partitioned between ethyl acetate and water. The organic phase was washed with water and evaporated to a froth (710 mg). This material was retreated with hydroxylamine as above to give a froth (800 mg) which was purified by preparative TLC (4% methanol in chloroform 22) and crystallisation from ethyl acetate/petrol to yield the title compound (220 mg), m.p. 176°–193°, $[\alpha]_D + 35.9°$.

PREPARATION 26

(Z)-11α-Amino-2β-ethoxy-5α-pregn-17(20)-en-3α-ol

A refluxing solution (under nitrogen) of (Z)-2β-ethoxy-3α-hydroxy-5α-pregn-17(20)-en-11-one 11-oxime (450 mg) in propan-1-ol (15 ml) was treated with pieces of Na (450 mg). When there was no trace of Na left the mixture was added to chilled water to give a fine precipitate which was collected by filtration.

The solid was dissolved in ethyl acetate, dried (Na$_2$SO$_4$) and evaporated to a froth which was partitioned between 2 N HCl and diethyl ether. The insoluble material which separated was collected by filtration and partitioned between ethyl acetate and 2 N NaOH solution. The organic phase was isolated, washed with water dried (Na$_2$SO$_4$) and evaporated to give a froth which was crystallised from petroleum ether to afford the title compound (110 mg), m.p. 65°–70°. $[\alpha]_D + 10°$.

PREPARATION 27

(Z)-11α-N,N-Dimethylamino-2β-ethoxy-5α-pregn-17(20)-en-3α-ol

A mixture of (Z)-11α-amino-2β-ethoxy-5α-pregn-17(20)-en-3α-ol (1.8 g), 40% aqueous formaldehyde (12 ml) and formic acid (1.2 ml) was kept at ca 100° for 5 minutes before pouring into aqueous NaHCO$_3$ solution. The precipitated solid was collected by filtration, washed with water and dissolved in ethyl acetate. Evaporation afforded a froth which was filtered through a plug of silica in ethyl acetate-petroleum ether (1:1). Recrystallisation from methanol-water then afforded the title compound, m.p. 63°–78°, $[\alpha]_D - 2°$.

EXAMPLE 1

11α-N,N-Dimethylamino-2β-ethoxy-17β-methyl-5α-androstan-3α-ol

A solution of 11α-amino-2β-ethoxy-17-methylene-5α-androstan-3α-ol (380 mg) in ethanol (10 ml) containing 10% Pd-C (200 mg) was stirred, under hydrogen, for 18 hours. Catalyst was removed by filtration through Kieselguhr and the solvent was evaporated in vacuo. The total crude product was dissolved in 98% formic acid (0.25 ml) and 37% aqueous formaldehyde (3 ml) and heated on the steam bath for 5 minutes. The cooled solution was diluted with sodium bicarbonate and extracted with ethyl acetate. The washed and dried (Na$_2$SO$_4$) extract was evaporated in vacuo and the residue was purified by preparative thin layer chromatography over silica to afford the title compound as a froth (100 mg), $[\alpha]_D - 12.8°$.

EXAMPLE 2

11α-N,N-Dimethylamino-2β-ethoxy-3α-hydroxy-5α-androstan-17-one

A solution of 11α-amino-2β-ethoxy-3α-hydroxy-5α-androstan-17-one (2.2 g) in 37% formaldehyde (12 ml) and 98% formic acid (1.2 ml) was heated on the steam bath for 3 minutes. The reaction mixture was diluted with sodium bicarbonate solution and extracted into ethyl acetate. The washed and dried extract was evaporated in vacuo to give a froth which was purified by column and preparative thin layer chromatography over silica (ethyl acetate:petroleum ether 1:1) and crystallization from aqueous ethanol to yield the title compound, m.p. 65°–68°, $[\alpha]_D + 41.7°$.

EXAMPLE 3

11α-N,N-Dimethylamino-2β-ethoxy-5α-androstan-3α-ol

A solution of 11α-N,N-dimethylamino-2β-ethoxy-5α-androst-16-en-3α-ol (181 mg) in ethyl acetate (20 ml) containing 10% palladium on charcoal (180 mg) was stirred at room temperature under hydrogen. The catalyst was removed by filtration through Kieselguhr and the solvent was evaporated in vacuo. Purification of the residue by preparative thin layer chromatography over silica (ethyl acetate:petroleum ether 1:1) and crystallization from aqueous methanol yielded the title compound (83 mg), m.p. 54°–59°, $[\alpha]_D - 16.7°$.

EXAMPLE 4

11α-N,N-Dimethylamino-16β,17β-epoxy-2β-ethoxy-5α-androstan-3α-ol

A solution of 17α-bromo-11α-N,N-dimethylamino-2β-ethoxy-5α-androstane-3α,16β-diol (212 mg) in methanol (33 ml) containing water (1.2 ml) was treated with a 40% solution of potassium carbonate (0.66 ml) and the mixture was refluxed. After 1 hour most of the solvent was evaporated and the residue was partitioned between ethyl acetate and water. The washed and dried (Na$_2$SO$_4$) organic layer was evaporated and the residue was purified by preparative thin layer chromatography over silica (ethyl acetate—petroleum ether 1:1) and crystallization from aqueous methanol to give the title compound (80 mg) m.p. 149°–151°, $[\alpha]_D + 6.7°$.

EXAMPLE 5

11α-N,N-Dimethylamino-17β-methyl-5α-androstan-3α-ol

A solution of 11α-amino-17-methylene-5α-androstan-3α-ol (417 mg) in ethanol (7 ml) containing 10% Pd-C (350 mg) was stirred under hydrogen for 1.5 hours. The catalyst was removed by filtration through a plug of Kieselguhr, the solvent was removed in vacuo and the residue was triturated with petroleum ether and the powder (255 mg) was collected by filtration. This material (240 mg) was dissolved in 37–40% aqueous formaldehyde (2.5 ml) containing 98–100% formic acid (0.2 ml) and the solution was heated on the steam bath for 7 minutes. The cooled solution was poured into 2 N-sodium hydroxide and the precipitated solid collected by filtration. Extraction of the filtrate with ethyl acetate afforded a further quantity (30 mg) of crystalline material which was combined with the major fraction. This material (260 mg) was purified by preparative thin layer chromatography (10% methanol in ethyl acetate) and crystallization from aqueous methanol to afford the title compound (183 mg), m.p. 150°–156°.

EXAMPLE 6

11α-N,N-Dimethylamino-3α-hydroxy-5α-androstan-17-one

11α-Amino-17,17-ethylenedioxy-5α-androstan-3α-ol (0.303 g) in formaldehyde (37–40% aqueous) (4 ml) was treated with formic acid (0.3 ml). The mixture was swirled until a solution was obtained then it was heated on a steam bath for 10 mins. The solution was cooled, diluted with water and treated with 2 N-hydrochloric acid. After 15 minutes the mixture was basified with 2 N-sodium hydroxide solution and the precipitated amorphous solid (0.272 g) was collected by filtration.

Crystallization from ethanol/water gave the title compound (0.198 g), m.p. 135°–136°. $[\alpha]_D +37.5°$.

EXAMPLES 7–14

Preparation of solutions of citric acid salts (Table 1)

The 11α-amine (1 part) was added to a solution of citric acid in water (about 90 parts) and the mixture was stirred until a clear solution was obtained. Water was added to give a solution containing about 10 mg free base per gm of solution. This solution was filtered through a membrane and its pH determined.

TABLE 1

| Example | Free base Example No. | wt. of free base (mg) | wt. of citric acid (mg) | Final wt. of solution (g) | conc. of solution mg free base/g soln. | pH |
| --- | --- | --- | --- | --- | --- | --- |
| 7 | 1 | 54 | 30 | 5.4 | 10 | 3.69 |
| 8 | 2 | 75 | 42 | 7.5 | 10 | 3.68 |
| 9 | 3 | 52 | 30 | 5.2 | 10 | 3.73 |
| 10 | 4 | 54 | 30 | 5.4 | 10 | 3.6 |
| 11 | 5 | 85 | 54 | 8.5 | 10 | 3.78 |
| 12 | 6 | 101 | 34 | 10 | 10.1 | 5.05 |
| 13 | 15 | 101 | 62 | 10.1 | 10 | 3.8 |
| 14 | 16 | 71 | 42 | 7.8 | 9.1 | 3.62 |

EXAMPLE 15

11α-N,N-Dimethylamino-5α-pregnan-3α-ol (Z)-11α-N,N-Dimethylamino-5α-pregn-17(20)-en-3α-ol (750 mg) in ethanol (25 ml) containing 10% Pd-C (511 mg) was stirred under hydrogen for 100 min. The catalyst was removed by filtration through Kieselguhr and the solvent evaporated in vacuo. Purification of the residue by filtration through a plug of silica in ethyl acetate-petroleum ether (2:1) and crystallisation from aqueous methanol gave the title compound (586 mg) m.p. 147°–150°, $[\alpha]_D -15.0°$

EXAMPLE 16

11α-N,N-Dimethylamino-2β-ethoxy-5α-pregnan-3α-ol (Z)-11α-N,N-Dimethylamino-2β-ethoxy-5α-pregn-17(20)-en-3α-ol (585 mg) in ethyl acetate (22 ml) containing 10% Pd-C (400 mg) was stirred under hydrogen. The catalyst was removed by filtration through Kieselguhr and the solvent evaporated in vacuo. Crystallisation of the residue from aqueous methanol gave the title compound (440 mg), m.p. 57°–59° C., $[\alpha]_D -4.8°$.

EXAMPLE A

Formulation of 11α-N,N-dimethylamino-2β-ethoxy-3α-hydroxy-5α-androstan-17-one for single dose injection, 5 mg/ml.

| | % w/v |
| --- | --- |
| Steroid | 0.50 |
| citric acid | 0.26 |
| sodium chloride | 0.80 |
| sodium hydroxide | to pH 4.5 |
| water for injections to | 100.00 |

Dissolve the citric acid in most of the water and add the steroid with stirring under a nitrogen blanket—once the steroid is in solution add the sodium chloride and dissolve. Then adjust the pH with sodium hydroxide solution and make the product up to volume. Clarify the solution by membrane filtration and fill under nitrogen into clean glass ampoules. Sterilise the sealed containers by moist heat.

We claim:

1. A compound of the formula

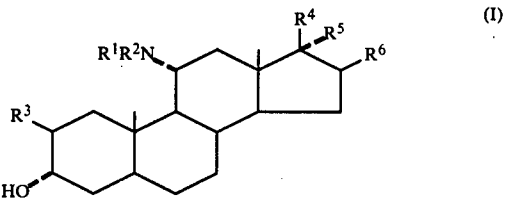

wherein:
one of $R^1$ and $R^2$ is a methyl group, the other group being a $C_{1-4}$ alkyl group, or $R^1$ and $R^2$ are both ethyl groups;
$R^3$ is a hydrogen atom or a $C_{1-4}$ alkoxy group; and
$R^4$ is a hydrogen atom or a methyl or ethyl group and $R^5$ and $R^6$ are hydrogen atoms; or $R^4$ and $R^6$ together represent an epoxide grouping and $R^5$ is a hydrogen atom; or $R^4$ and $R^5$ together represent an oxo group and $R^6$ is a hydrogen atom;
and the acid addition salts thereof.

2. A compound as claimed in claim 1 which possesses a 5α-hydrogen atom.

3. A compound as claimed in claim 2 wherein $R^3$ is an alkoxy group.

4. A compound as claimed in claim 3 wherein $R^3$ is an ethoxy group.

5. A compound as claimed in claim 1 wherein $R^1$ and $R^2$ are both methyl groups.

6. A compound as claimed in claim 1 wherein $R^4$ and $R^5$ together represent an oxo group and $R^3$ is an alkoxy group, and wherein a 5α-hydrogen atom is present.

7. A compound as claimed in claim 1, said compound being:
11α-N,N-dimethylamino-2β-ethoxy-17β-methyl-5α-androstan-3α-ol;
11α-N,N-dimethylamino-2β-ethoxy-5α-androstan-3α-ol;
11α-N,N-dimethylamino-16β,17β-epoxy-2β-ethoxy-5α-androstan-3α-ol; or
11α-N,N-dimethylamino-17β-methyl-5α-androstan-3α-ol;
or a physiologically acceptable acid addition salt thereof.

8. A compound as claimed in claim 1, said compound being 11α-N,N-dimethylamino-2β-ethoxy-3α-hydroxy-5α-androstan-17-one or a physiologically acceptable acid addition salt thereof.

9. A compound as claimed in claim 1 in the form of its hydrochloride or citrate salt.

10. A pharmaceutical composition consisting essentially of a compound as claimed in claim 1 and a pharmaceutical carrier or excipient.

11. A composition as claimed in claim 10 wherein said compound is formulated in a parenterally acceptable vehicle.

12. A composition as claimed in claim 11 which is an aqueous solution of a physiologically acceptable acid addition salt of the active compound.

13. A method of inducing anaesthesia in man or animals which comprises administering to the subject an effective amount of a compound as claimed in claim 1.

* * * * *